United States Patent
Ryu et al.

(10) Patent No.: US 8,319,961 B2
(45) Date of Patent: Nov. 27, 2012

(54) APPARATUS TO PERFORM A NON-CONTACT TEST OF A SEMICONDUCTOR PACKAGE

(75) Inventors: Chang-Hyun Ryu, Cheonan-si (KR); Ssang-Gun Lim, Daejeon (KR); Dong-Hae Son, Asan-si (KR); Poom-Seong Park, Asan-si (KR)

(73) Assignees: SAMSUNG Electronics Co., Ltd., Suwon-si (KR); INTEKPLUS Co., Ltd., Daejeon (KR)

( * ) Notice: Subject to any disclaimer, the term of this patent is extended or adjusted under 35 U.S.C. 154(b) by 332 days.

(21) Appl. No.: 12/632,960

(22) Filed: Dec. 8, 2009

(65) Prior Publication Data

US 2010/0141937 A1 Jun. 10, 2010

(30) Foreign Application Priority Data

Dec. 8, 2008 (KR) .......................... 10-2008-0124144

(51) Int. Cl.
*G01N 21/00* (2006.01)

(52) U.S. Cl. ................ 356/237.5; 356/237.1; 356/237.6

(58) Field of Classification Search ..... 356/237.1–237.6
See application file for complete search history.

(56) References Cited

U.S. PATENT DOCUMENTS

| 7,276,719 B2* | 10/2007 | Schwarz ............... 250/559.36 |
| 7,433,055 B2* | 10/2008 | Schwarz et al. ............. 356/600 |
| 7,511,806 B2* | 3/2009 | Hamamatsu et al. ....... 356/237.2 |
| 2005/0254065 A1* | 11/2005 | Stokowski .................... 356/601 |
| 2008/0144014 A1* | 6/2008 | Vollrath et al. .................. 356/73 |

FOREIGN PATENT DOCUMENTS

| JP | 2001243821 A | * | 9/2001 |
| JP | 2002-267415 | | 9/2002 |
| JP | 2004327361 A | * | 11/2004 |
| JP | 2006-041167 | | 2/2006 |
| KR | 20-0176154 | | 1/2000 |
| KR | 2001-37417 | | 5/2001 |

* cited by examiner

*Primary Examiner* — Tarifur Chowdhury
*Assistant Examiner* — Isiaka Akanbi
(74) *Attorney, Agent, or Firm* — Stanzione & Kim, LLP

(57) ABSTRACT

An apparatus to test a semiconductor package includes a vertical illuminator to supply vertical illumination in the same axial direction as a measurement target and a vertical image unit to capture a vertical image of the measurement target so that a testing apparatus may 2-dimensionally determine information on the shape, size, or position of a solder ball. An inclined illuminator may supply inclined illumination in a different axial direction from the measurement target, and an inclined image capture unit may capture a side image of the measurement target so that the testing apparatus may 3-dimensionally determine information on a state of contact of the solder ball with the ball land. The inclined image capture unit may include a color camera using color information, thereby markedly increasing test reliability and yield.

29 Claims, 10 Drawing Sheets

FIG. 7

|  | RED VALUE | GREEN VALUE | BLUE VALUE |
|---|---|---|---|
| NON-WET | 139 | 92 | 31 |
| WET | 96 | 86 | 96 |

APPARATUS TO PERFORM A NON-CONTACT TEST OF A SEMICONDUCTOR PACKAGE

CROSS-REFERENCE TO RELATED APPLICATIONS

This application claims priority under 35 U.S.C. §119 to Korean Patent Application No. 10-2008-0124144, filed Dec. 8, 2008, the contents of which are incorporated herein by reference in their entirety.

BACKGROUND

1. Field of the Invention

Example embodiments relate to a semiconductor package testing apparatus, and more particularly, to an apparatus to test a stacked semiconductor package, or multi-stack package (MSP), which provides vertical and inclined images from various angles to obtain a stereoscopic effect and employs color information from a color camera to improve test reliability and shorten a test time.

2. Description of the Related Art

With an increase in integration density of electronic/information apparatuses, demands for high-pin-count semiconductor packages have increased. Thus, a vast amount of research is being conducted on Array Type semiconductor packages, such as ball-grid-array (BGA) packages, which satisfy the demands for the high-pin-count semiconductor packages and reduce chip sizes and fabrication costs. In recent years, a fine-pitch BGA package, which is a kind of chip scale package, has been developed.

In addition, brisk development of stacked semiconductor packages (MSP) in which chips are stacked, packages are stacked, or chips and packages are stacked together has progressed to increase the capacity and integration density of semiconductor devices.

In general, a semiconductor device is an essential component for computers and household electrical appliances. The semiconductor device necessarily undergoes a precise test after production and before shipment. A semiconductor device requires a far higher degree of precision than other components. Therefore, a very small defect in an internal element or external appearance of the semiconductor device may be detrimental to its performance.

A defect in lead or ball, which occurs during the assembly of a printed circuit board (PCB), affects an external appearance of a semiconductor device. Accordingly, a process of testing the state of a lead or ball of a semiconductor device including a PCB on which a ball grid array (BGA) is mounted is being regarded as very important among semiconductor-device testing processes.

SUMMARY

Example embodiments provide a semiconductor package testing apparatus, which obtains an image of a multi-stack package (MSP) in a vertical direction to determine information on size, shape, or position of a solder ball, information on generation of particles, and information on cracks or other losses in the solder ball.

Example embodiments also provide a semiconductor package testing apparatus, which obtains an image of an MSP in a lateral direction to determine 3-dimensional information on a contact portion between a solder ball and a ball land when a non-wet defect between the solder ball and the ball land is tested.

Example embodiments further provide a semiconductor package testing apparatus, which employs color information to improve test reliability when a contact of a solder ball with a ball land is tested in a noncontact manner.

Additional aspects and utilities of the present general inventive concept will be set forth in part in the description which follows and, in part, will be obvious from the description, or may be learned by practice of the general inventive concept.

Features and/or utilities of the present general inventive concept may be realized by a semiconductor package testing apparatus including a vertical illuminator to supply vertical illumination in the same axial direction as a measurement target, an inclined illuminator to supply inclined illumination in a different axial direction from the measurement target, a vertical image capture unit to capture a vertical image of the measurement target, and an inclined image capture unit to capture an inclined image of the measurement target.

The vertical illumination to illuminate the measurement target may travel along the same light path as the light reflected by the measurement target, and the inclined illumination may travel along a light path to the measurement target that is different than the light path of light reflected by the measurement target.

The measurement target may be a stacked semiconductor package. Each of the vertical and inclined illuminators may illuminate both sides of the measurement target, and each of the vertical and inclined image capture units may capture inclined images of the measurement target.

The vertical image of the measurement target may contain information on the sizes, shapes, and positions of a solder ball and a ball land that are connected to each other to electrically connect a plurality of packages constituting the stacked semiconductor package. The inclined image of the measurement target may contain information on a bonding state between a solder ball and a ball land that are connected to each other to electrically connect a plurality of packages constituting the stacked semiconductor package.

The vertical illuminator may be a plate including a plurality of light emitting diodes (LEDs). The plate may be installed parallel to a light path of irradiation light emitted toward the measurement target and a light path of reflection light reflected by the measurement target, and a half mirror functioning as a beam splitter may be installed at a predetermined tilt angle in front of the plate. The half mirror may change a light path of irradiation light emitted by the LEDs in a vertical direction and allow the reflection light to pass therethrough and be incident to the vertical image unit.

The tilting illuminator may have a hemispheric dome shape having an inner surface on which a plurality of LEDs is mounted. Also, the tilting illuminator may have a central opening to allow irradiation light incident to the measurement target and reflection light reflected by the measurement target to pass therethrough.

The vertical image capture unit may determine self-information on the shape, size, or position of a solder ball, peripheral information on generation of particles, and information on a bonding state between the solder ball and a ball land.

The inclined image capture unit may be installed at an inclined angle with respect to the measurement target to capture an image of a contact portion between a solder ball and a ball land. A reflection mirror may be further disposed on one side of the inclined image capture unit to allow the reflection light reflected by the measurement target to be incident to the inclined image capture unit. The inclined image capture unit may be installed at an inclined angle with respect to an optical axis of reflection light re-reflected by the reflection mirror.

The semiconductor package testing apparatus may further include a condensing lens and an optical angle shifter. The condensing lens may be disposed in front of the inclined image capture unit and condense the incident reflection light. The optical angle shifter may be disposed between the inclined image capture unit and the condensing lens and may shift a direction of the reflection light re-reflected by the reflection mirror such that the light path of the reflection light is consistent with the inclined image capture unit. When reflection light reflected at two spots of the measurement target is re-reflected by the reflection mirror and incident to the inclined image capture unit, the optical angle shifter may compensate for a difference in length between two light paths starting from the two spots.

The inclined image capture unit may include a color camera using color information to determine whether or not a solder ball is bonded to a ball land. The inclined image capture unit may extract colors from the color information and determine whether or not the solder ball is bonded to the ball land based on the extracted colors. The solder ball may be formed of lead (Pb) that takes on a blue color, and the ball land may be formed of copper (Cu) that takes on a red color. When the lead melts during a reflow process, the lead may be attached to the copper and the copper may be concealed so that only the blue color may be detected. Conversely, when the lead does not melt during the reflow process, the lead may not be attached to the copper and the copper may be exposed so that both the red and blue colors may be detected.

The color camera may obtain light reflected from the surface of the measurement target as color information and extract a red (R) value, a blue (B) value, and a green (G) value from the obtained color information. Thus, when subtracting the B value from the R value gives a value higher than a critical value, the color camera may determine that the solder ball and the ball land are in a non-wet state. Also, when subtracting the B value from the R value gives a critical value or lower, the color camera may determine that the solder ball and the ball land is in a wet state.

The vertical and inclined illuminators and the vertical and inclined image capture units may be mounted in a case, and a portion of a bottom surface of the case corresponding to the measurement target may be opened to allow irradiation light emitted toward the measurement target and reflection light reflected by the measurement target to pass therethrough. The case may further include an illumination mount on which the vertical and inclined illuminators are mounted. The illumination mount may be disposed on the opened bottom surface and have an opening formed in the center of each of top and bottom surfaces thereof to allow illumination to pass therethrough. The vertical illuminator may be vertically mounted on an outer top surface of the illumination mount, and the inclined illuminator may be installed inside the illumination mount. The case may include a camera mount having at least an opened portion of a bottom surface through which the irradiation light and the reflection light pass. Also, the vertical image capture unit and the inclined image capture unit may be installed at a ceiling of the camera mount not to interrupt light paths of the irradiation light and the reflection light.

Features and/or utilities of the present general inventive concept may also be realized by a semiconductor package testing apparatus including an inclined illuminator installed above a measurement target and having a hemispheric shape, the inclined illuminator having a plurality of LEDs disposed on a portion other than an opening formed in the center thereof to supply illumination to the measurement target, an inclined image capture unit configured to receive reflection light reflected by the measurement target and capture a side image of the measurement target, a reflection mirror installed at an inclined angle on one side of the inclined image capture unit to guide the reflection light reflected by the measurement target into the inclined image capture unit, and a condensing lens installed in front of the inclined image capture unit and configured to condense incident reflection light.

The measurement target may be a stacked semiconductor package in which a ball land to which a solder ball is attachable is formed on a first surface of a printed circuit board (PCB), and the solder ball is bonded to the ball land during a reflow process and functions as an input/output terminal of the PCB. The inclined image capture unit may be installed at a predetermined angle with respect to an optical axis of reflection light re-reflected by the reflection mirror to capture an image of a contact portion between the solder ball and the ball land.

The semiconductor package testing apparatus may further include an optical angle shifter disposed between the inclined image capture unit and the condensing lens. The optical angle shifter may shift a direction of the reflection light. When reflection light reflected at two spots of the measurement target is re-reflected by the reflection mirror and incident to the inclined image capture unit, the optical angle shifter may compensate for a difference in length between two light paths starting from the two spots.

The inclined image capture unit may obtain light reflected from the surface of the measurement target as color information, extract a red (R) value and a blue (B) value from the color information, and determine whether or not the solder ball is bonded to the ball land based on the color information. When the solder ball and the ball land are in a wet state, the solder ball formed of lead (Pb) may melt during a reflow process and be bonded to the ball land formed of copper (Cu) and the ball land formed of the copper may be concealed so that subtracting the B value from the R value gives a critical value or lower. Conversely, when the solder ball and the ball land are in a non-wet state, the solder ball formed of lead may not melt during the reflow process and the ball land formed of the copper may be exposed so that subtracting the B value from the R value gives a value higher than a critical value. In this case, the critical value may range from 0 to 255 on condition of 8 bits.

Features and/or utilities of the present general inventive concept may also be realized by a testing apparatus including a first illumination device to illuminate a target area of a tested device, the first illumination device providing illumination to the target area such that light from the first illumination device contacts the target area along an axis parallel to a center length axis of the tested device, a second illumination device to illuminate a target area of a tested device, the second illumination device providing illumination to the target area such that light from the second illumination device contacts the target area along an axis that is not parallel to a center length axis of the tested device, a first image capture device to receive light from the first illumination device reflected off of the target area, and a second image capture device to receive light from the second illumination device reflected off of the target area. The center length axis of the tested device may define a first direction.

The second image capture device may include a color-receptive image capture device.

The first illumination device may include a substantially flat plate and a plurality of light emitting diodes mounted to the plate.

The second illumination device may include a substantially dome-shaped structure having a hole at a peak of the dome to permit light to pass through the hole and a plurality of light emitting diodes mounted to an inside surface of the dome-shaped structure.

The testing apparatus may further include a beam-splitting mirror positioned along a light path between the first illumination device and the target area, to reflect light from the first illumination device toward the target area, and to pass light from the target area toward the first image capture device. The beam-splitting mirror may be positioned at a 45° angle with respect to the first direction.

The testing apparatus may further include a mirror to reflect light that has been reflected off of the target area from an inclined angle to be parallel with respect to the first direction, and the mirror may reflect the light from the tested device toward the second image capture device.

The testing apparatus may further include a condensing lens to receive and condense the light from the mirror and an optical angle shifter to receive the condensed light from the condensing lens and to adjust the light to provide a focused image to an image-reception end of the second image capture device.

The second image-capture unit may be positioned to have a center length axis that is not parallel to the first direction.

The testing apparatus may further include a case, and the first and second illumination devices and first and second image capture devices may be mounted to be located on an inside of the case to be fixed with respect to the case.

The testing apparatus may further include a camera mounting structure having a height less than a height of the case, and the first and second image capture devices may be mounted to an inner surface of a top side of the camera mounting structure.

The testing apparatus may further include an illumination unit mounting structure mounted to an inside surface of a lower portion of the case, and the first and second illumination devices may be mounted to the illumination unit mounting structure.

Features and/or utilities of the present general inventive concept may also be realized by a method of testing a tested device, the method including positioning the tested device to have a length axis parallel to a first direction, emitting a first light to travel in the first direction to contact a test area of the tested device, capturing a first image of the test area generated by the first light reflected off of the test area of the tested device at a 180° angle with respect to the first direction, emitting a second light to travel in a second direction that is not parallel to the first direction, and capturing a second image of the test area generated by the second light reflected off of the test area at a second angle that is not parallel to the first direction.

The method may further include capturing color data of the second image. The color data may correspond to red, green, and blue color of the test area.

Capturing the second image may include capturing light that travels parallel to the first direction.

A light path of the light that travels parallel to the first direction may be adjusted to enter an image-receiving surface of an image-capture device at an angle that is not parallel to the first direction.

Emitting the first light may include emitting the first light in a second direction perpendicular to the first direction and reflecting the first light off of a beam-splitting mirror to travel parallel to the first direction toward the target area.

Capturing the first image may include capturing light reflected off of the target area and passed through the beam-splitting mirror.

Capturing the second image may include capturing the second light reflected off of the test area at an angle that is not parallel to the first direction and reflected off of a mirror to travel in a direction parallel to the first direction.

The method may include providing a first illumination device to emit the first light, a second illumination device to emit the second light, a first image-capture device to capture the first image, and a second image capture device to capture the second image, mounting the first illumination device, the second illumination device, the first image-capture device, and the second image capture device to a case having a hole in a bottom of the case to pass light, and positioning the tested device outside the case adjacent to the hole.

BRIEF DESCRIPTION OF THE DRAWINGS

The above and/or other aspects of the present general inventive concept will become apparent and more readily appreciated from the following description of the exemplary embodiments, taken in conjunction with the accompanying drawings, in which:

Example embodiments are described in further detail below with reference to the accompanying drawings. It should be understood that various aspects of the drawings may have been exaggerated for clarity:

FIG. 7 is a table showing comparison results of red, green, and blue values extracted using color information based on a bonding state according to an example embodiment;

DETAILED DESCRIPTION OF THE EMBODIMENTS

Figure 1:
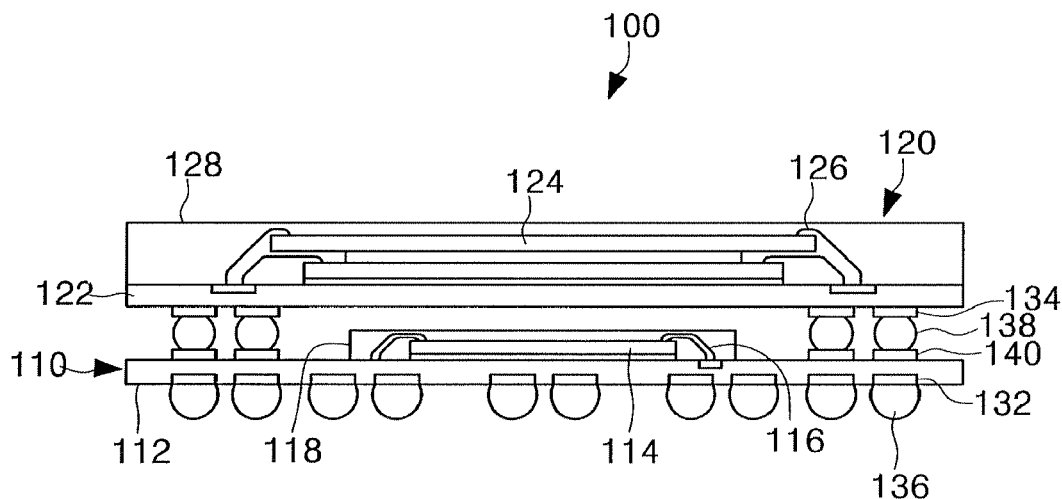
FIG. 1 is a lateral view of a semiconductor package according to an example embodiment.
Figure 2:
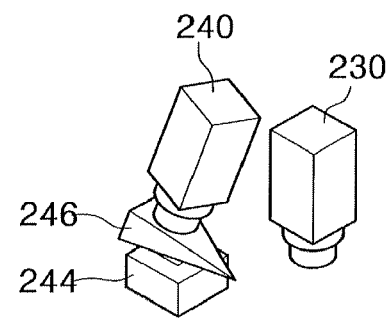
FIG. 2 is a cross-sectional view of a semiconductor package testing apparatus according to an example embodiment.
Figure 2:
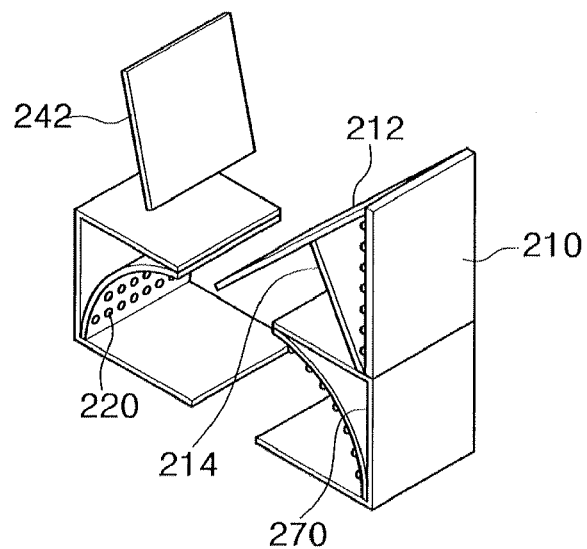

Reference will now be made in detail to the embodiments of the present general inventive concept, examples of which are illustrated in the accompanying drawings, wherein like reference numerals refer to the like elements throughout. The embodiments are described below in order to explain the present general inventive concept by referring to the figures.

FIG. 1 is a cross-sectional view of a stacked semiconductor package that may be analyzed by a testing device according to an example embodiment.

Referring to FIG. 1, a stacked semiconductor package, or multi-stack package (MSP), 100 may include a first semiconductor package 110 and a second semiconductor package 120 stacked on the first semiconductor package 110.

The first semiconductor package 110 may include a single first chip 114 adhered onto a first printed circuit board (PCB) 112. The single first chip 114 may be electrically connected to the first PCB 112 by first bonding wires 116 and encapsulated using a first molding resin 118. The second semiconductor package 120 may include a plurality of second chips 124 adhered to and stacked on a second PCB 122. The plurality of second chips 124 may be electrically connected to the second PCB 122 by second bonding wires 126 and encapsulated using a second molding resin 128.

A plurality of first ball lands 132 may be located on a bottom surface of the first PCB 112, and a plurality of second ball lands 134 may be located on a bottom surface of the second PCB 122. First solder balls 136 functioning as external terminals may be bonded to the first ball lands 132, respectively, and second solder balls 138 functioning as external terminals may be bonded to the second ball lands 134.

Meanwhile, third ball lands 140 may be disposed on a top surface of the first PCB 110. When the second semiconductor package 120 is stacked on the first semiconductor package 110, the second solder balls 138 may be bonded onto the third ball lands 140. Specifically, a predetermined flux may be coated on the third ball lands 140, and the first and second semiconductor packages 110 and 120 may be thermally bonded to each other under pressure such that the second solder balls 138 of the second PCB 122 are positioned on the third ball lands 140, respectively. Thus, the second semiconductor package 120 may be stacked on the first semiconductor package 110 and, simultaneously, the first and second semiconductor packages 110 and 120 may be electrically connected to each other by the second solder balls 138.

However, the stacked semiconductor package 100 may suffer a non-wet defect between the second solder ball 138, which electrically connects the first and second semiconductor packages 110 and 120, and the third ball land 140 of the first semiconductor package 110.

For example, a non-wet defect may occur due to negligent management of a flux with a predetermined viscosity to be coated on the third ball land 140 to bond the second solder ball 138 to the third ball land 140. Alternatively, an excessively small amount of the flux coated on the third ball land 140 may result in a non-wet defect.

Since it is impossible to detect these non-wet defects by means of current equipment, an operator should perform a total inspection. Therefore, it is absolutely necessary to develop an apparatus to test a stacked semiconductor package in a non-contact manner to detect whether or not the stacked semiconductor package has a non-wet defect.

As shown in FIGS. 2, 3A, 3B, 4A, and 4B, a semiconductor package testing apparatus 200 according to the present general inventive concept may include a vertical illuminator 210, an inclined illuminator 220, a vertical image capture unit 230, and an inclined image capture unit 240.

Figure 9:
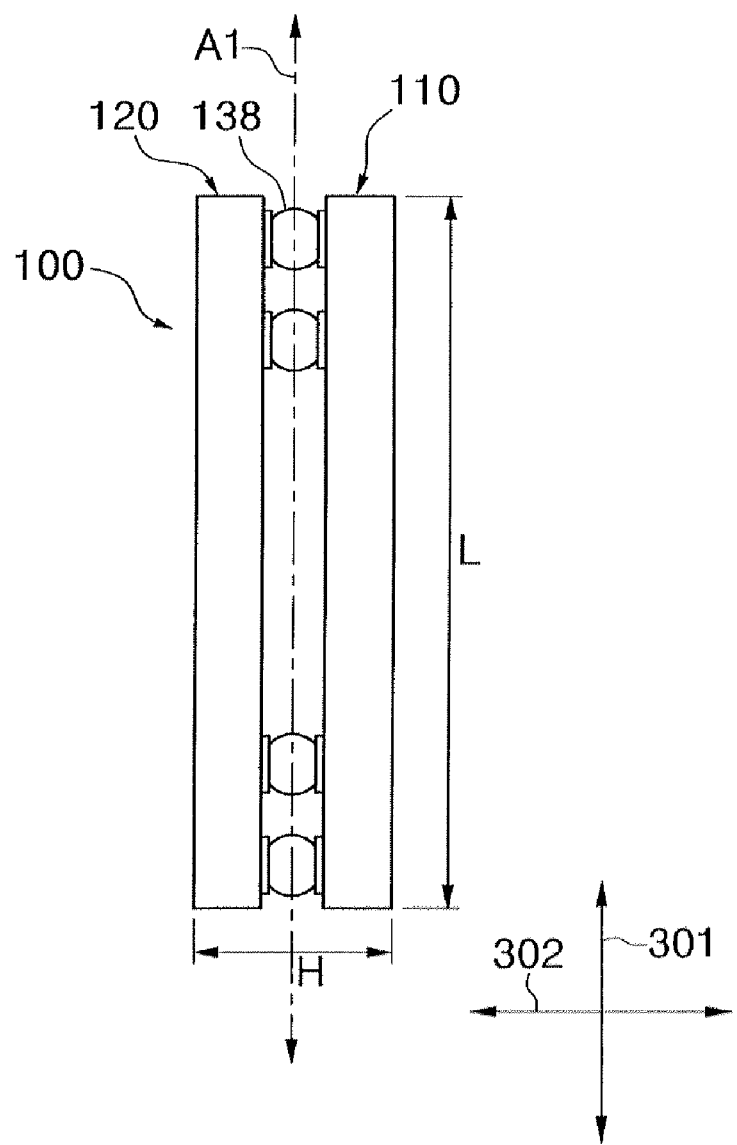
FIG. 9 illustrates a length axis of the stacked semiconductor package.

In the description to follow, the term "vertical" is used to describe a relationship between various elements of the general inventive concept including the package testing apparatus 200 and the stacked semiconductor package 100. However, the package testing apparatus 200 and the stacked semiconductor package 100 may be arranged in any direction, such as horizontally, upside-down, or at any other predetermined angle. As illustrated in FIG. 9, the "vertical" direction in this description corresponds to a first direction 301 parallel to a length axis A1 of the stacked semiconductor package 100.

Figure 3A:
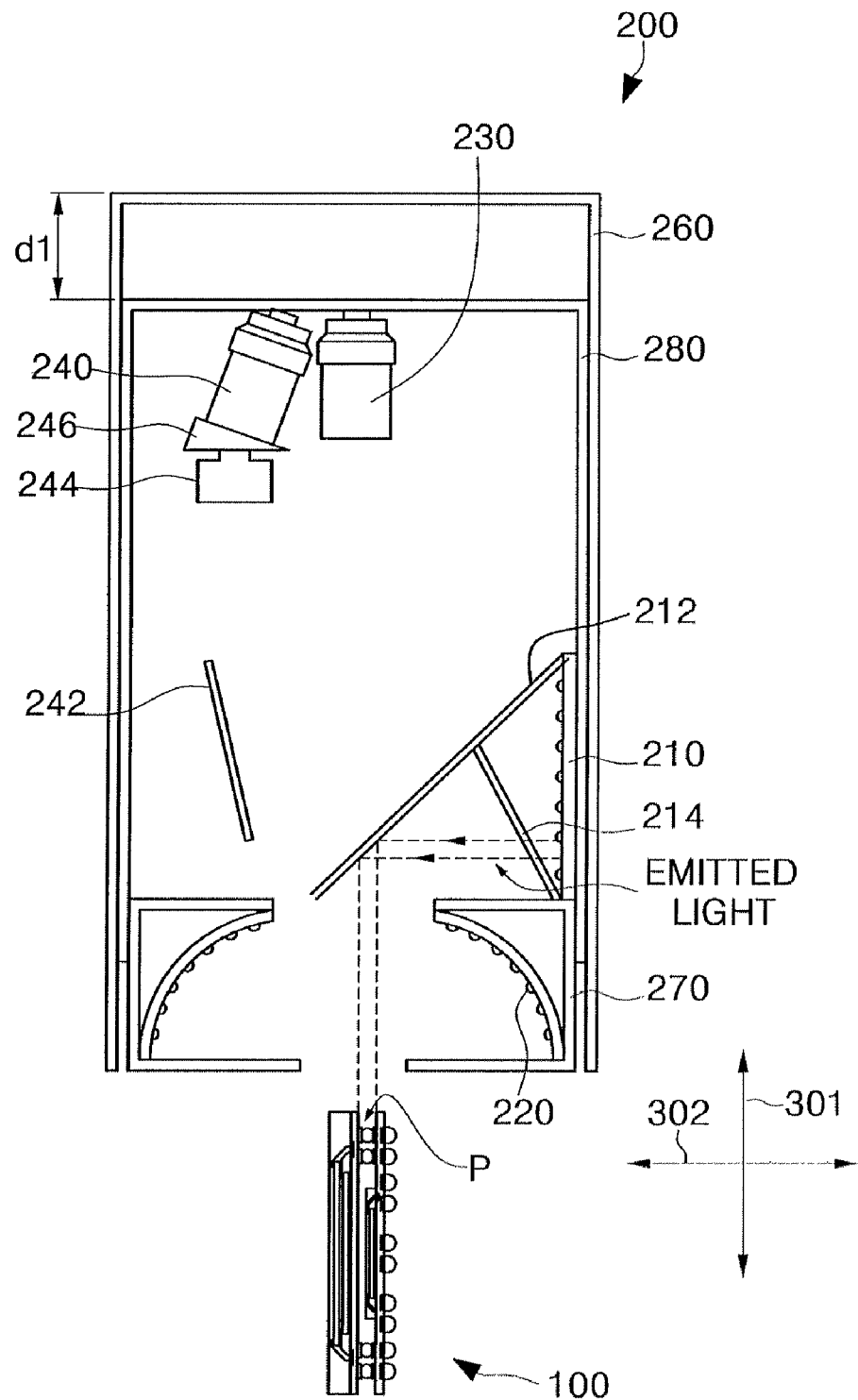
FIGS. 3A and 3B are side plan views of a semiconductor package testing apparatus according to an example embodiment.

As illustrated in FIG. 3A, the vertical illuminator 210 emits light in a horizontal direction 302 toward a beam-splitting mirror 212. The beam-splitting mirror 212 reflects the light to travel in a vertical direction 301 onto the measurement target or target area P, which may be a portion of the stacked semiconductor package 100. For example, the measurement target, or target area, P may be a connection comprising a second ball land 134, a second solder ball 138, and a third ball land 140. The stacked semiconductor package 100 may be positioned vertically, or may be positioned to expose the measurement target P to light traveling along an axis parallel to the vertical direction 301.

Figure 3B:
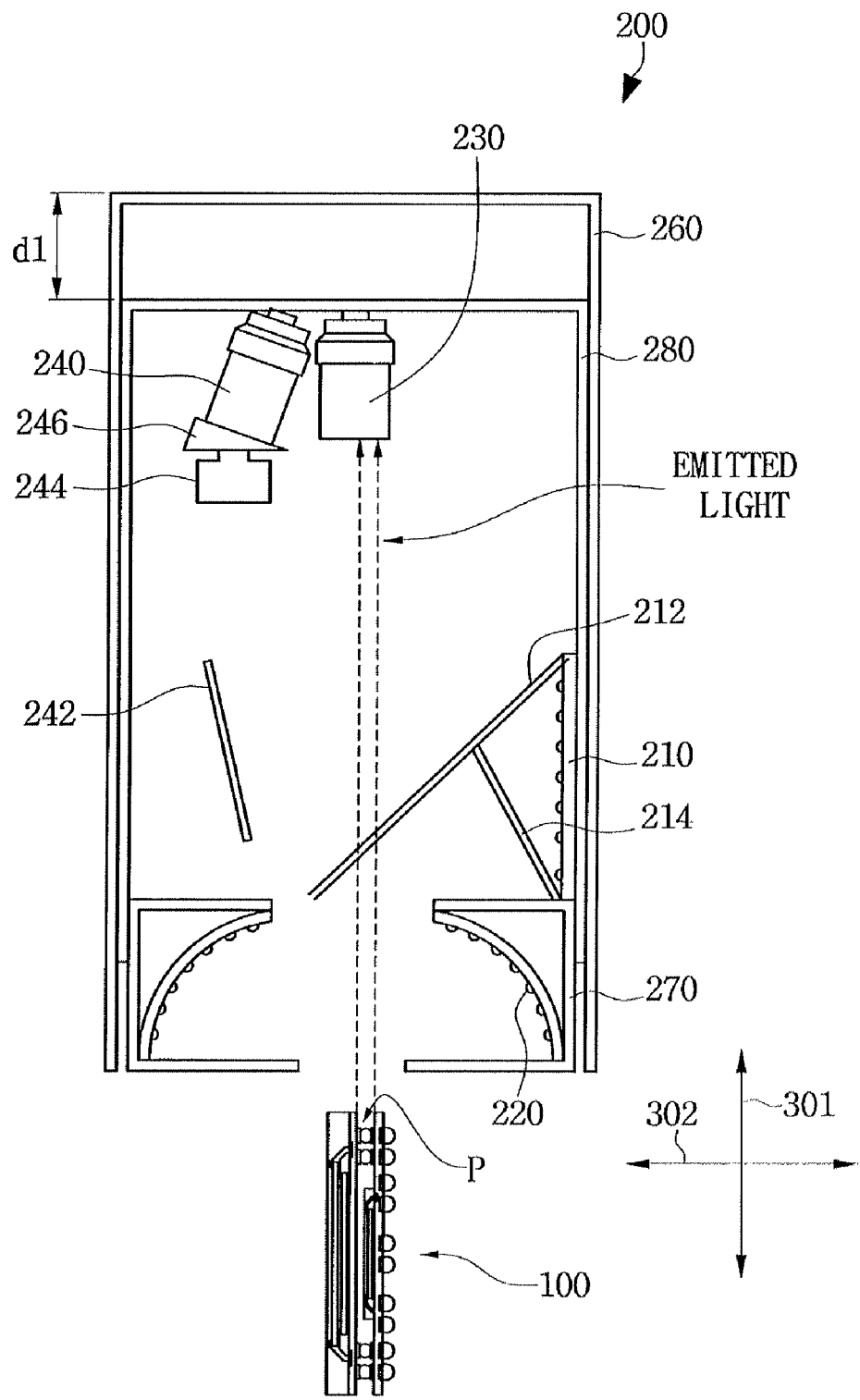

As illustrated in FIG. 3B, the light transmitted from the beam-splitting mirror 212 to the measurement target P may then be reflected off the measurement target P in the vertical direction 301 towards the vertical image capture unit 230. The light may pass through the beam-splitting mirror 212 and to the vertical image capture unit 230 for analysis.

Figure 4A:
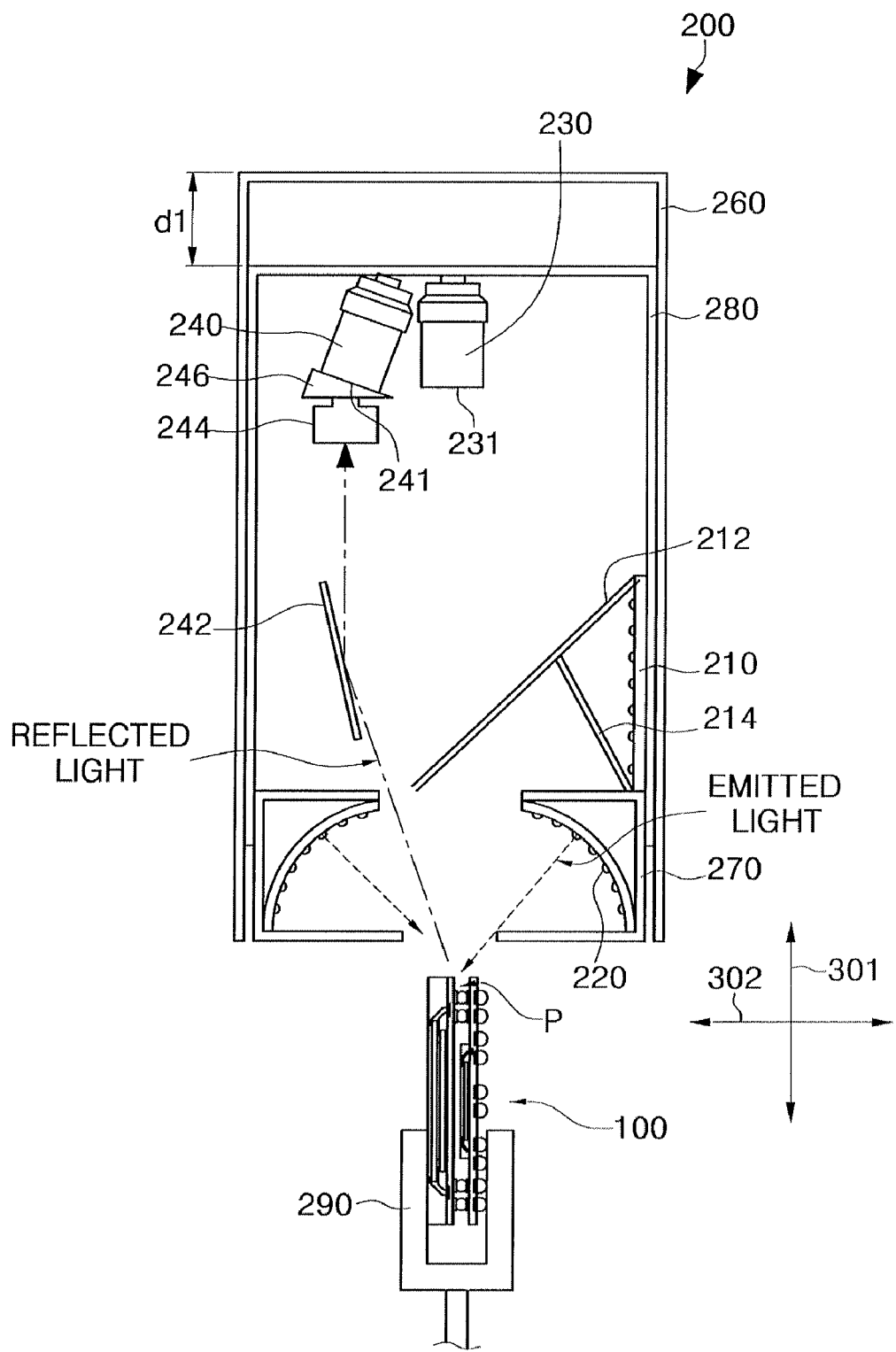
FIGS. 4A and 4B illustrate side plan views of the semiconductor package testing apparatus.

As illustrated in FIG. 4A, the inclined illuminator 220 may emit illumination to the measurement target P at an angle that is inclined with respect to the direction 301. Light from the inclined illuminator 220 may reflect off a surface of the measurement target P at an angle so that the reflected light travels in a direction that is not parallel to vertical 301. The light may travel parallel to a center axis a3 of the inclined image capture unit 240 at an image-receiving end 241 of the inclined image capture unit 240

The vertical illuminator 210, the inclined illuminator 220, the vertical image capture unit 230, and the inclined image capture unit 240 may be mounted in a case 260 to provide illumination and to capture an image at a predetermined distance and angle. The case 260 may have a rectangular shape with an inner space in which the vertical illuminator 210, the inclined illuminator 220, the vertical image capture unit 230, and the inclined image capture unit 240 are mounted. A portion of a bottom surface of the case 260 corresponding to a position of the measurement target P may be opened to allow light emitted from the illuminators 210, 220 and reflected from the measurement target P to pass therethrough.

The measurement target P may be located below the case 260. The stacked semiconductor package 100 may be mounted in a holder 290 that may be moved horizontally 302 or vertically 301 with respect to the testing apparatus 200. Alternatively, the testing apparatus 200 may be moved with respect to the holder 290.

Sizes, shapes, or positions of a solder ball 138 and a ball land 140 of the measurement target P may be measured by illuminating the measurement target P with the vertical and inclined illuminators 210, 220 and analyzing the light reflected from the measurement target 100 with the vertical and inclined image capture units 230, 240. The vertical illuminator 210 and the inclined illuminator 220 may illuminate one or multiple sides of the measurement target P.

The testing apparatus according to the present inventive concept may measure not only the shape of a ball-grid-array (BGA) ball or defects in a ball-grid-array ball but also the shape of lead used to bond a semiconductor chip to a PCB substrate and a defect in the lead. However, for brevity, the present example embodiment is limited to the measurement target P including the solder ball 138 and ball land 140 of the stacked semiconductor package 100.

An illumination mount 270 on which the vertical illuminator 210 and the inclined illuminator 230 are mounted may be provided on the opened bottom surface of the case 260. The illumination mount 270 may include an opening to allow light to pass therethrough.

The vertical illuminator 210 may be vertically mounted on a top surface of the illumination mount 270. Alternatively, the vertical illuminator 210 may be mounted directly on an inner sidewall of the case 260. The vertical illuminator 210 is offset from a straight line between the measurement target P and the vertical image unit 230 so as to avoid blocking light paths between the measurement target P and the vertical image unit 230. The vertical illuminator 210 may be a plate having a surface on which a plurality of light emitting diodes (LEDs) is mounted.

Since the vertical illuminator 210 is positioned to the side of the measurement target P, the beam-splitting mirror 212 is positioned in the vertical direction 301 above the measurement target P to reflect a path of light from the vertical illuminator 210 to travel toward the measurement target P and to allow reflected light from the measurement target P to pass through the beam-splitting mirror 212 to travel toward the vertical image capture unit 230. The beam-splitting mirror 212 may be installed at an angle of about 45° with respect to vertical 301. Furthermore, an inter-mirror 214 may be further provided between the beam-splitting mirror 212 and the vertical illuminator 210 to prevent irradiation light emitted from the vertical illuminator 210 from being totally reflected by the half mirror 212. In this case, since light passing through the inter-mirror 214 or a coating mirror may be emitted in all directions, total reflection of light may be prevented.

The inclined illuminator 220 may be mounted in the illumination mount 270. The inclined illuminator 220 may have a hemispheric dome shape having an inner surface on which a plurality of LEDs is mounted. An opening through which irradiation light and reflection light pass may be formed in the center of the dome-shaped inclined illuminator 220. Since the LEDs are disposed and irradiate light in a hemispheric shape, the inclined illuminator 220 may provide illumination to the measurement target P from various angles.

A camera mount 280 may be further provided in the case 260. At least a portion of a bottom surface of the camera mount 280 may be open to facilitate mounting the camera mount 280 to the illumination mount 270. The vertical image capture unit 230 and the inclined image capture unit 240 may be installed on a ceiling of the camera mount 280 such that the vertical image capture unit 230 and the inclined image capture unit 240 may perform respective specific functions without interrupting the irradiation light path from the illuminators 210, 220 to the measurement target P and the reflection light path from the measurement target P to the image capture units 230, 240. Using the camera mount 280, the vertical image capture unit 230 and the inclined image capture unit 240 may be efficiently installed in a minimum space without affecting or being affected by other components.

The vertical image capture unit 230 may be installed toward a lower portion of the case 260 or the camera mount 280. More specifically, the vertical image capture unit 230 may be installed closer to the measurement target P than the upper side of the case 260 or the camera mount 280. For example, the vertical image capture unit 230 may be installed on an upper side of the camera mount 280 that may separated from an upper side of the case 260 by a predetermined distance d1. The vertical image capture unit 230 may obtain information on the measurement target P based on light that is irradiated by the vertical illuminator 210. For example, the vertical image capture unit 230 may determine information on the shape, size, or position of the solder ball 138 or information on a bonding state between the solder ball 138 and the ball land 140 based on light reflected from the measurement target P.

The vertical image capture unit 230 may also determine whether or not the solder ball 138 suffers a crack, deformation, or another loss based on information on the shape of the solder ball 138. Furthermore, after a reflow process, the vertical image capture unit 230 may determine whether the solder ball 138 is bonded to the ball land 140 based on the shape of the solder ball 138.

Figure 5:
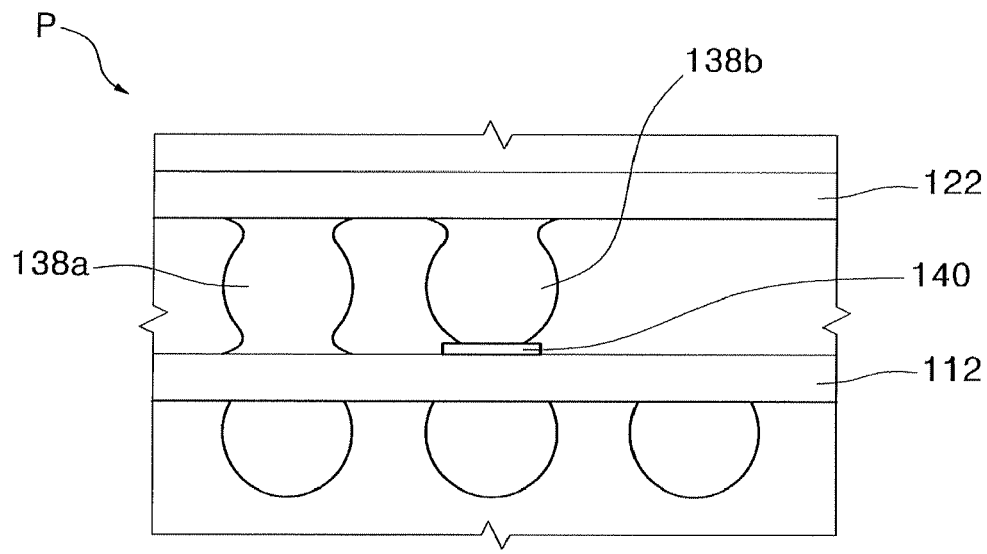
FIG. 5 is a partial perspective view of an inclined image of a semiconductor package according to an example embodiment.

FIG. 5 illustrates an image of the measurement target P captured by the vertical image capture unit 230. In FIG. 5, the vertical image capture unit 230 determines that two different kinds of solder balls 138 exist in the measurement target P. The first solder ball 138a has a jar shape, in which the solder covers each of the second ball land 134 and the third ball land 140. The second solder ball 138b has a spherical shape. The vertical image capture unit 230 is able to determine that, since the solder ball 138b has a spherical shape, the solder ball 138b is not properly bonded to the ball land 140. In contrast, since solder ball 138a has a jar shape as a result of an annealing process, the solder ball 138a is bonded to the ball land 140. In addition, the vertical image unit 230 may determine whether or not the solder ball 138 or the ball land 140 has particles that cause an electrical short. Accordingly, it can be determined whether or not the solder ball 138 is defective based on the position, height, or shape of the solder ball 138.

Meanwhile, since a semiconductor packaging process is carried out at a high temperature, thermal stress may be applied to the PCBs and semiconductor chips. A warping defect may occur due to a difference in the coefficient of thermal expansion between a PCB and a semiconductor chip. Thus, a solder ball 138 attached to a predetermined region of a first PCB may not be bonded to a ball land 140 of a second PCB due to the warping of the first PCB. In addition, even if one side of a solder ball 138 is bonded to a ball land 140, the other side of the solder ball 130 may be shifted so that the solder ball 138 cannot function as an input/output terminal.

As described above, information on the shape of the solder ball 138 and information on a bonding state between the solder ball 138 and the ball land 140 may be analyzed using the vertical image capture unit 230. However, most non-wet defects cannot be detected by the vertical image capture unit 230. For example, when one side of the solder ball 138 is bonded to the ball land 140 and the other side of the solder ball 138 is shifted, even if the stacked semiconductor package 100 has a substantial non-wet defect, the vertical image capture unit 230 cannot detect the shifted side of the solder ball 138. To overcome this restriction, the semiconductor package testing apparatus 200 may further include the inclined image capture unit 230 capable of capturing an image from various angles.

The inclined image capture unit 240 may be installed on one side of the vertical image capture unit 230 and may capture an angled image of the measurement target P. As described above, the vertical image unit 230 may detect only the side of the measurement target P and cannot easily detect a region including the ball land 140 disposed on a plane surface of a PCB. In other words, the vertical image capture unit 230 may capture a 2-dimensional image but not a 3-dimensional image. Since non-wet defects are mainly detected at a contact portion between the solder ball 138 and the ball land 140, the testing apparatus 200 may detect the non-wet defect by capturing an image at a predetermined tilt angle.

In addition, the inclined image capture unit 240 may detect more objectively whether or not the solder ball 138 is bonded to the ball land 140 based on color information of a captured image. This is due to the fact that information on the shape of the solder ball 138 always has a measurement error. Thus, when a non-wet defect between the solder ball 138 and the ball land 140 is detected based on the side image of the measurement target P, the inclined image capture unit 240 may employ the color information of the captured image.

Typically, the solder ball 138 is a ball-shaped material that connects PCBs and transmits an electrical signal. The solder ball 138 may melt during a reflow process, thus deforming its ball shape. For example, a typical solder ball 138 may be formed of eutectic tin-lead obtained by mixing tin (Sn) and lead (Pb) in a ratio of 63% to 37%. Thus, the lead takes on a bluish gray color. The ball land 140 may be formed of conductive copper (Cu), which takes on a reddish yellow color. When the lead melts during the reflow process, the shape of the solder ball 138 may be deformed so that the lead may be attached to the surface of the ball land 140 formed of copper. Accordingly, when the lead efficiently melts and the solder ball 138 is normally bonded to the ball land 140, the reddish yellow color of the ball land 140 cannot be detected, but only the bluish gray color of the solder ball 138 may be detected.

Accordingly, the inclined image capture unit 240 may include a color camera, which may obtain light reflected from the surface of the measurement target P as color information and extract red (R), blue (B), and green (G) values from the color information.

When subtracting a B value from the extracted R value gives a positive (+) value, the testing apparatus 200 may determine that the stacked semiconductor package 100 is defective. This is because when the solder ball 138 is not annealed at a required temperature, the solder ball 138 cannot be bonded to the ball land 140. In other words, when the solder ball 138 does not melt and cover the ball land 140, the ball land 140 may not turn gray but still remain yellow. When subtracting the B value from the extracted R value gives a value other than a positive (+) value, the testing apparatus 200 may determine that the stacked semiconductor package 100 is normal. For example, when the R value is equal to the B value or subtracting the B value from the R value gives a negative (−) value, it may be determined that the stacked semiconductor package 100 is normal.

Here, neither a positive (+) value nor a negative (−) value refers to an absolute value. For example, since the intensity of each of an R value, a B value, and a G value ranges from 0 to 255 on condition of 8 bits, a user may determine a desired critical value within the given range. In the present general inventive concept, a defective stacked semiconductor package may be distinguished from a normal multi-stack package. Thus, when an stacked semiconductor package has a value higher than a critical value, it is determined that the solder ball 138 and the ball land 140 are in a non-wet state, and when the stacked semiconductor package has the critical value or lower, it is determined that the solder ball 138 and the ball land 140 are in a wet state.

Figure 6:
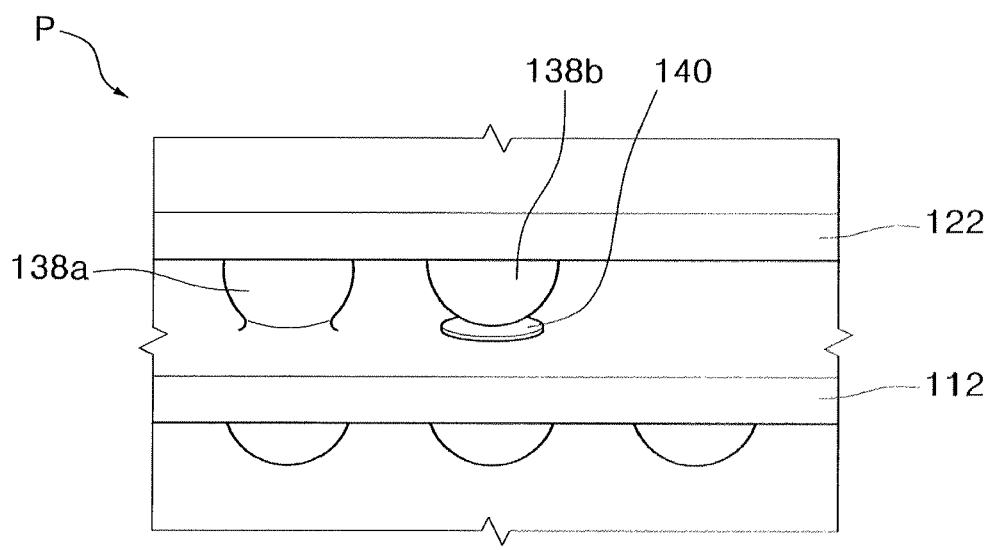
FIG. 6 is a partial lateral view of a vertical image of a semiconductor package according to an example embodiment.

FIG. 6 illustrates an image of the measurement target P captured by the inclined image capture device 240. In FIG. 6, the solder ball 138*b* is in a non-wet state with the ball land 140. Specifically, the solder ball 138*b* formed of lead (Pb) does not cover the ball land 140 formed of copper (Cu) so that the ball land 140 is exposed. As illustrated in the chart of FIG. 7, the right image may have an R value of 139, a G value of 92, and a B value of 31. Thus, the R value is greater than the B value.

Referring again to FIG. 6, the solder ball 138*a* is in a wet state with a corresponding ball land (not shown). Specifically, the solder ball 138*a* formed of lead covers the ball land formed of copper. As illustrated in the chart of FIG. 7, the left image may have an R value of 96, a G value of 86, and a B value of 96. Thus, the R value is equal to the B value.

Referring again to FIG. 4A, a reflection mirror 242 may be positioned within the case 260 to reflect light from the measurement target P toward the inclined image capture unit 240. A condensing lens 244 may be positioned in front of the inclined image capture unit 240 to condense light reflected off the measurement target P and to direct the condensed light toward the inclined image capture unit 240.

An optical angle shifter 246 may be positioned between the inclined image capture unit 240 and the condensing lens 244 to adjust a light path of reflection light condensed by the condensing lens 244. The optical angle shifter 246 may be a beam shaping prism, which functions to shift a direction of reflection light condensed by the condensing lens 244 at a predetermined angle and to collimate the reflection light. Since an optical axis of light reflected from the measurement target P is inclined at a predetermined angle with respect to vertical 301, when the inclined image capture unit 240 is positioned in a vertical direction, the tilting image unit 240 may be out of focus. The optical angle shifter 246 adjusts the light path of the reflected light to bring the image received by the inclined image capture unit into focus.

Figure 8:
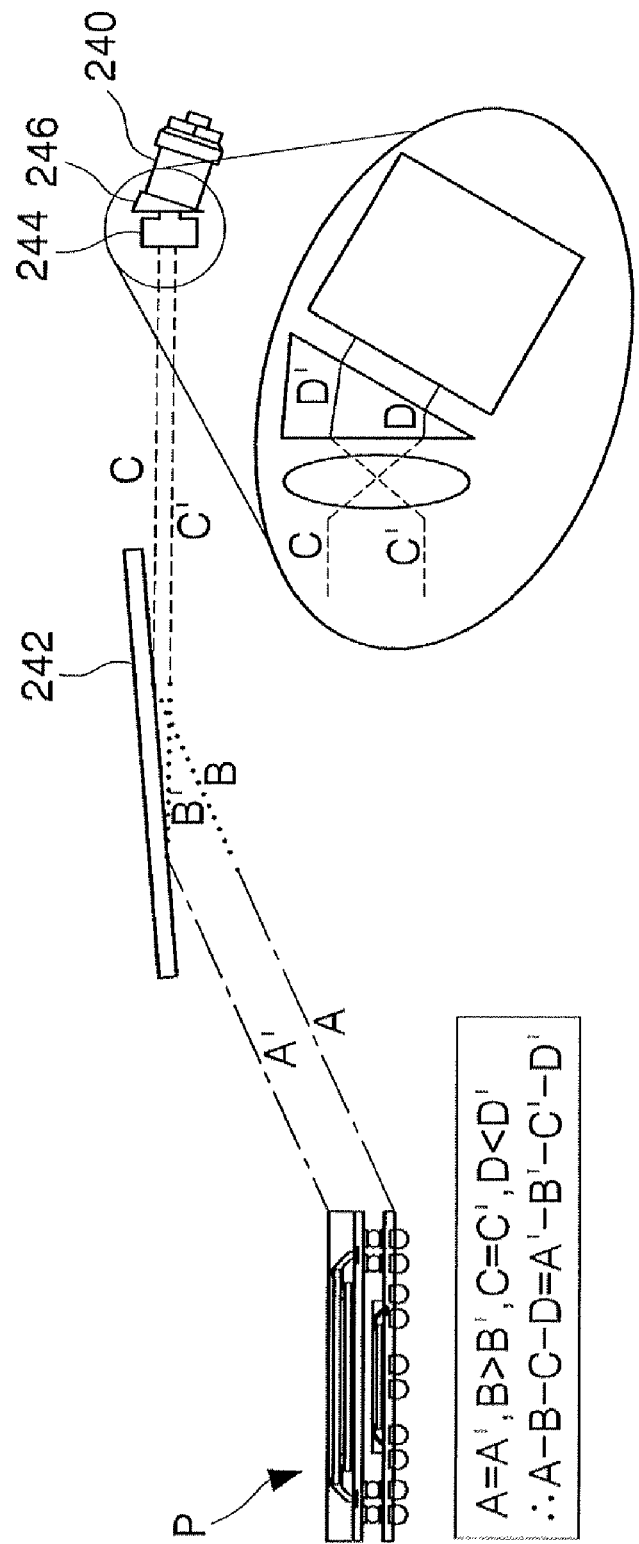
FIG. 8 illustrates a lateral view of a reflection light path in the semiconductor package testing apparatus.

That is, as shown in FIG. 8, since the space in an image corresponding to the measurement target P has a predetermined volume, when reflection light reflected at two points of the measurement target P is re-reflected by the reflection mirror 242 and incident to the inclined image capture unit 240, the length of a light path from a first point of the measurement target P to the camera may be different from that of a light path from a second point of the measurement target P to the inclined image capture unit 240. That is, a light path A-B-C may be longer than a light path A'-B'-C' (a light path A-B-C>a light path A'-B'-C'). When the inclined image capture unit 240 is installed along an optical axis of reflection light, the inclined image capture unit 240 may capture a distorted image different from an original shape of the measurement target P due to the difference in length between the two light paths. Accordingly, the inclined image capture unit 240 should be installed at an angle with respect to the optical axis of the reflection light to capture an image reflecting the original shape of the measurement target P. In this case, the optical angle shifter 246 may be required to compensate for a difference in length between the two light paths (a light path D<a light path D') and collimate reflection light (a light path A-B-C-D=a light path A'-B'-C'-D').

Figure 4B:
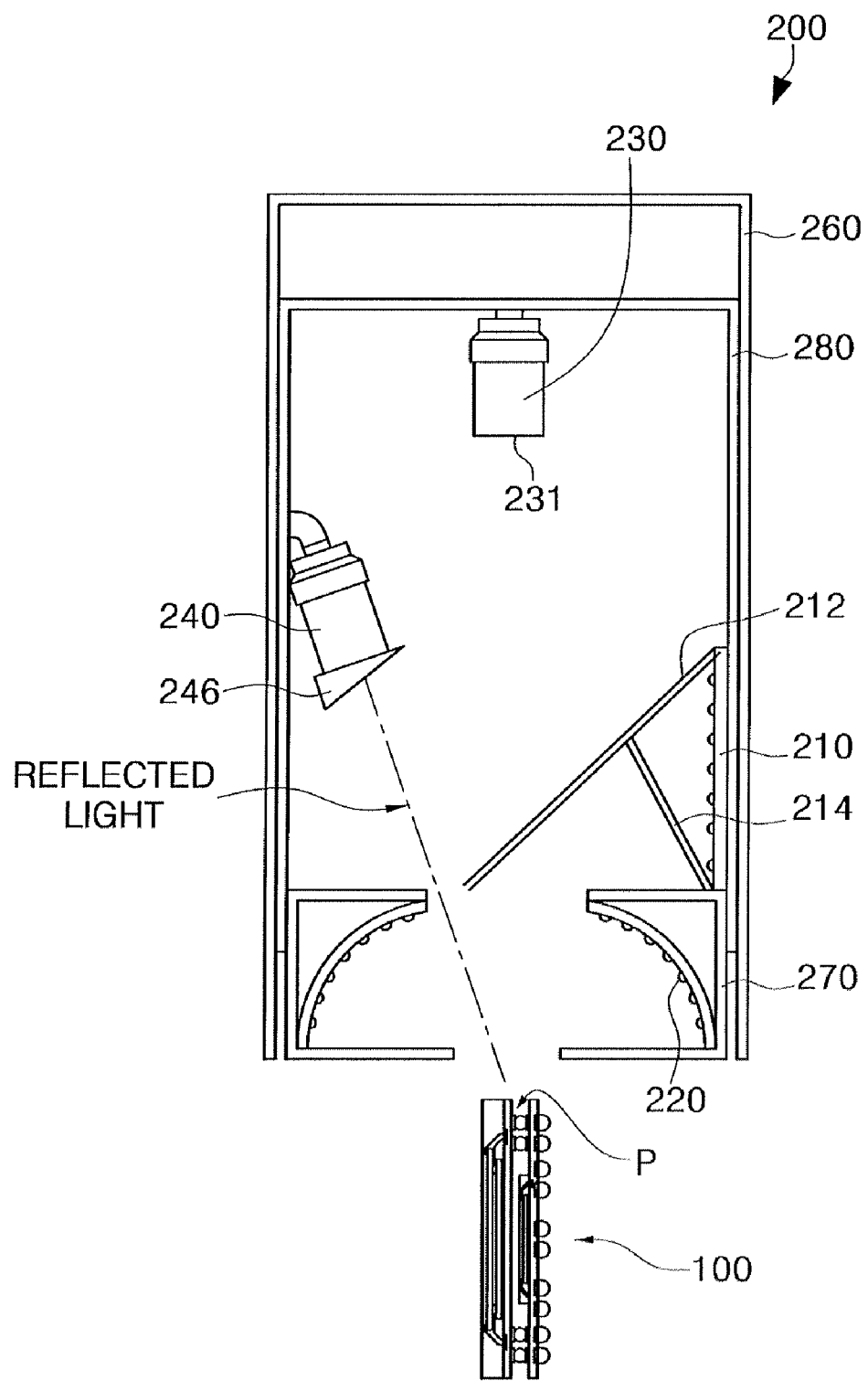

FIG. 4B illustrates the inclined image capture unit 240 being mounted on a side wall of the camera mount 280. The image capture unit 240 may be mounted at an angle with respect to vertical 301 or may be mounted such that a center axis of the image capture unit 240 is parallel to a vertical 301 axis. An optical angle shifter 246 may adjust the reflected light to prevent image distortion into the inclined image capture unit 240.

Figure 10A:
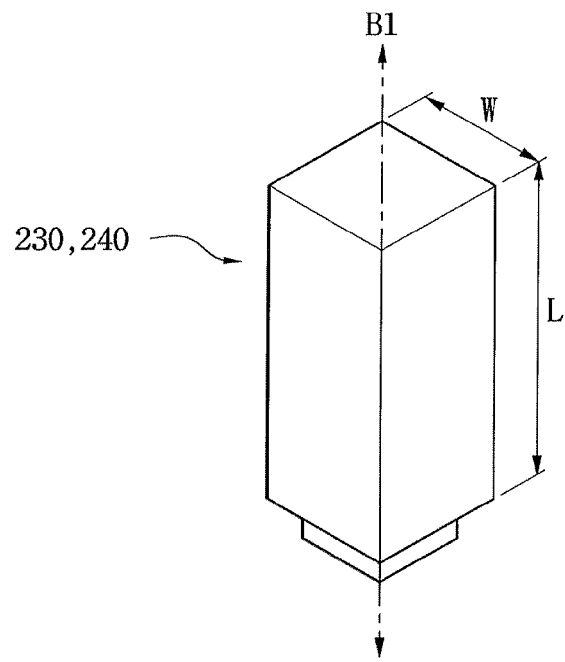
FIGS. 10A and 10B illustrate the length axis of image-capture devices.
Figure 10B:
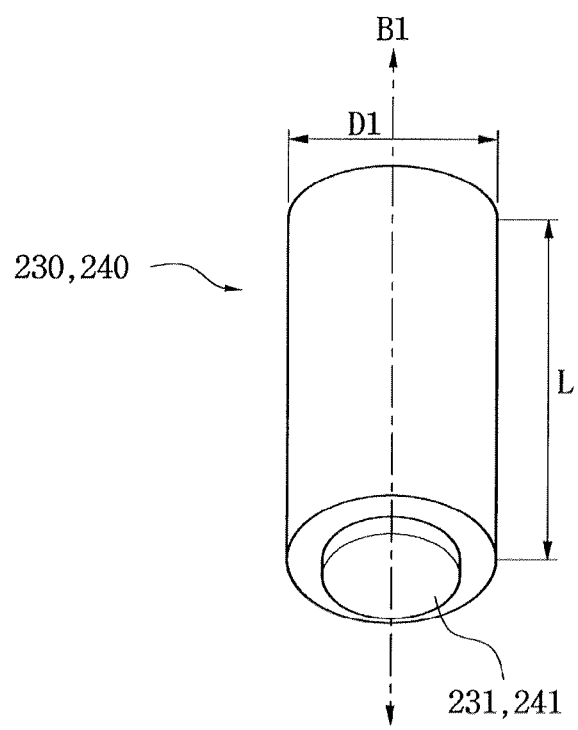

FIGS. 9, 10A, and 10B illustrate center length axes of the stacked semiconductor chip package 100 and the image capture devices 230, 240.

As illustrated in FIG. 9, a stacked semiconductor chip package 100 has a length direction L corresponding to a length of a semiconductor chip and a height direction H corresponding to a height of the first semiconductor package 110, the second semiconductor package 120, and the second solder balls 138 between the first and second semiconductor packages. Details of the stacked semiconductor package 100 are described above with respect to FIG. 1 and are omitted from the description of FIG. 9.

A center length axis is defined as an axis A travelling in a length direction of the stacked semiconductor package 100 at a location that is substantially half the height H of the semiconductor package 100. The center length axis A may also correspond to half of a width (not shown) of the semiconductor chip package 100. When a stacked semiconductor package includes more than first and second semiconductor packages, the center length axis A corresponds to half the height of all of the semiconductor packages and the intervening solder balls, connections, and/or filling of the stacked semiconductor package. As illustrated in FIG. 9, the center length axis A of the stacked semiconductor package 100 is substantially parallel to the flat surfaces of the semiconductor chips in the semiconductor package 100.

When the stacked semiconductor package 100 is positioned beneath a testing unit 200, it may be positioned vertically, as shown in FIG. 9, so that the center axis A may correspond to a vertical direction 301 and an end solder ball 138 may be illuminated and imaged.

FIG. 10A illustrates an image capture device 230, 240 having substantially rectangular sides. The image capture device 230, 240 has a length L corresponding to a distance between a rear side and an image-capture side. The image capture device 230, 240 has a width W corresponding to an edge of the rear side or the image-capture side. A length axis B1 of the image capture device 230, 240 is defined as an axis that is substantially at a center of each opposite side and each opposite corner. The length axis B1 travels in a length L direction of the image capture device 230, 240 and intersects each of the rear side and the image-capture side. When the rear side and image capture side are flat, the axis B1 intersects the sides at a right angle.

Since the image capture device 230, 240 may have any shape, and may not have flat sides, the length axis B1 may be defined as travelling in a length direction of the image capture device 230, 240 an intersecting the image-capture side at a right angle, if flat, and at a tangent at its apex, if curved.

FIG. 10B illustrates an image capture device 230, 240 having a substantially cylindrical shape. The length L of the image capture device 230, 240 may be defined as a distance from the rear side to the image-capture side 231, 241, and a diameter D1 or width of the cylinder may be defined as a diameter of either end of the image capture device 230, 240. The center axis B1 of the image capture device 230, 240 may be defined as a line travelling from a rear of the image capture device 230, 240 to the image-capture side 231, 241 of the image capture device 230, 240 being substantially equidistant from the curved cylindrical sides. When the image-capture side 231, 241 is flat, the length axis B1 may be perpendicular to the image-capture side 231, 241, and when the image-capture side 231, 241 is curved, the length axis B1 may be tangential to an apex of the image-capture side 231, 241.

As discussed above with respect to FIGS. 3A and 3B, the stacked semiconductor package 100 may be positioned vertically, so that its length axis A1 is parallel to the length axis B1 of the vertical image-capture unit 230. In addition, the length axis A1 of the stacked semiconductor package may be co-linear with the length axis B1 of the vertical image-capture unit 230.

Hereinafter, a process of testing a semiconductor package according to an example embodiment will be described.

The vertical illuminator 210 and the inclined illuminator 220 may be simultaneously driven or they may be driven one-at-a-time.

When the vertical illuminator 210 is driven, light emitted by the vertical illuminator 210 may pass through the inter-mirror 214, be reflected by the beam-splitting mirror 212 at a right angle, and be transmitted to the measurement target P. The light may be reflected by the measurement target P and the reflected light may pass through the beam-splitting mirror 212 to be captured by an image capturing unit (not shown) of the vertical image capture unit 230, which includes a camera. The captured image may be converted into a digital image signal and transmitted to a controller, which may analyze the digital image signal and determine whether or not the corresponding measurement target P is defective.

That is, the vertical image unit 230 may process light re-reflected by the measurement target P and produce an image, and may determine the size, shape, and position of the solder ball 138 based on the image.

When the inclined illuminator 220 is driven, light emitted by the inclined illuminator 220 may be irradiated toward the measurement target P from various angles. Part of reflection light that is irradiated to the measurement target P at a predetermined tilt angle may be reflected off of the measurement target P and re-reflected by the reflection mirror 242 toward the image capturing unit of the inclined image capture unit 240. The condensing lens 244 may condense the light re-reflected by the reflection mirror 242, and the optical angle shifter 246 may compensate for a light path of the condensed light. Thus, the inclined image capture unit 240 may receive collimated light and may capture an image of the measurement target P.

Accordingly, an image of the measurement target P may be captured at a predetermined tilt angle so that a contact portion between the solder ball 138 and the ball land 140 may be tested based on the angled image. Also, it may be determined more accurately whether the solder ball 138 is bonded to the ball land 140 using the color camera as the inclined image capture unit 240. In other words, a degree of reflow between the solder ball 138 and the ball land 140 may be measured based on color information.

As explained thus far, a semiconductor package may suffer a non-wet defect between a solder ball and a ball land due to warping or inclination of the solder ball with respect to the ball land. In this case, the non-wet defect may be detected in a noncontact manner, and an image of the semiconductor package may be captured from various angles, thereby obtaining a substantial stereoscopic image. In particular, semiconductor packages may be tested using color information, thereby enhancing test reliability and simplifying a testing process.

As described above, a semiconductor package testing apparatus according to the present inventive concept may have the following effects.

First, since irradiation light emitted by a vertical illuminator is at a right angle to reflection light reflected by a measurement target, a wider range of information including not only on the shape or position of a solder ball but also peripheral information on generation of particles may be obtained. In particular, information on a bonding state between the solder ball and a ball land, such as a solder joint crack, may be detected based on a vertical image of the measurement target.

Second, an image of a contact portion between the solder ball and the ball land may be captured from various angles so that substantial stereoscopic information on the measurement target may be obtained.

Third, an angled image of the measurement target may be employed to obtain stereoscopic information that cannot be obtained using a vertical image. In this case, information on color reflected from the surface of the measurement target may be extracted, and it may be determined whether or not the solder ball is reliably bonded to the ball land based on the extracted information. As a result, measurement errors may be minimized, and test reliability may be markedly improved.

Although a few embodiments of the present general inventive concept have been illustrated and described, it will be appreciated by those skilled in the art that changes may be made in these embodiments without departing from the principles and spirit of the general inventive concept, the scope of which is defined in the appended claims and their equivalents.

What is claimed is:

1. A semiconductor package testing apparatus comprising:
a vertical illuminator to illuminate a measurement target of a measured device from a vertical direction parallel to a length axis of the measured device;
an inclined illuminator to illuminate the measurement target at an inclined angle with respect to the length axis of the measured device, the inclined illuminator having a hemispheric dome shape having an inner surface on which a plurality of LEDs are mounted, and having a central opening to allow light from the inclined illuminator to travel to the measurement target and to allow light reflected by the measurement target to pass through the central opening;
a vertical image capture unit to capture an image of the measurement target from light travelling vertically directly from the measurement target; and
an inclined image capture unit to capture an image of the measurement target from light travelling at an inclined angle with respect to the length axis of the measured device immediately upon being reflected from the measurement target.

2. The apparatus of claim 1, wherein the measurement target is positioned so that light received from the vertical illuminator travels parallel to the light from the vertical illuminator that is reflected from the measurement target, and
light received from the inclined illuminator is not parallel to light from the inclined illuminator that is reflected from the measurement target.

3. The apparatus of claim 2, wherein the measurement target is a multi-stack package (MSP), each of the vertical and inclined illuminators illuminates both sides of the measurement target, and each of the vertical and inclined illuminators captures side images of the measurement target.

4. The apparatus of claim 3, wherein the vertical image of the measurement target contains information on the sizes, shapes, and positions of a solder ball and a ball land that are connected to each other to electrically connect a plurality of packages constituting the stacked semiconductor package.

5. The apparatus of claim 3, wherein the side image of the measurement target contains information on a bonding state between a solder ball and a ball land that are connected to each other to electrically connect a plurality of packages constituting the stacked semiconductor package.

6. The apparatus of claim 3, wherein the vertical image unit determines self-information on the shape, size, or position of a solder ball, peripheral information on generation of particles, and information on a bonding state between the solder ball and a ball land.

7. The apparatus of claim 3, wherein the inclined image capture unit is installed at a tilt angle with the measurement target to capture an image of a contact portion between a solder ball and a ball land, and
a reflection mirror is further disposed on one side of the inclined image capture unit to allow the reflection light reflected by the measurement target to be incident to the inclined image capture unit.

8. The apparatus of claim 7, wherein the inclined image capture unit is installed at a tilt angle with an optical axis of reflection light re-reflected by the reflection mirror.

9. The apparatus of claim 8, further comprising:
a condensing lens disposed in front of the inclined image capture unit and configured to condense the incident reflection light; and
an optical angle shifter disposed between the inclined image capture unit and the condensing lens and configured to shift a direction of the reflection light re-reflected by the reflection mirror such that the light path of the reflection light is consistent with the inclined image capture unit.

10. The apparatus of claim 9, wherein when reflection light reflected at two points of the measurement target is re-reflected by the reflection mirror and incident to the inclined image capture unit, the optical angle shifter compensates for a difference in length between two light paths starting from the two spots.

11. The apparatus of claim 3, wherein the inclined image capture unit includes a color camera using color information to determine whether or not a solder ball is bonded to a ball land.

12. The apparatus of claim 11, wherein the inclined image capture unit extracts colors from the color information and determines whether or not the solder ball is bonded to the ball land based on the extracted colors,
the solder ball is formed of lead (Pb) that takes on a blue color, and the ball land is formed of copper (Cu) that takes on a red color,
when the lead melts during a reflow process, the lead is attached to the copper and the copper is concealed so that only the blue color is detected, and
when the lead does not melt during the reflow process, the lead is not attached to the copper and the copper is exposed so that both the red and blue colors are detected.

13. The apparatus of claim 12, wherein the color camera obtains light reflected from the surface of the measurement target as color information and extracts a red (R) value, a blue (B) value, and a green (G) value from the obtained color information,
the color camera determines that the solder ball and the ball land are in a non-wet state when subtracting the B value from the R value gives a value higher than a critical value, and
the color camera determines that the solder ball and the ball land are in a wet state when subtracting the B value from the R value gives a critical value or lower.

14. The apparatus of claim 1, wherein:
the vertical illuminator is a plate including a plurality of light emitting diodes (LEDs),
the plate is positioned vertically so as to be parallel to the length axis of the measured device, and a beam splitter is installed at a predetermined tilt angle in front of the plate, and
the beam splitter changes a light path of light emitted by the LEDs to travel in a vertical direction and allows the light reflected from the measurement target to pass through the beam-splitter.

15. The apparatus of claim 1, wherein the vertical and inclined illuminators and the vertical and inclined image capture units are mounted in a case, and a portion of a bottom surface of the case corresponding to the measurement target is opened to allow irradiation light emitted toward the measurement target and reflection light reflected by the measurement target to pass therethrough,
the case further comprises an illumination mount on which the vertical and inclined illuminators are mounted, the illumination mount disposed on the opened bottom surface of the case and having an opening formed in the center of each of top and bottom surfaces thereof to allow illumination to pass therethrough,
the vertical illuminator is vertically mounted on an outer top surface of the illumination mount, and the inclined illuminator is installed inside the illumination mount, the case includes a camera mount having at least an opened portion of a bottom surface through which the irradiation light and the reflection light pass, and the vertical image unit and the inclined image capture unit are installed at a ceiling of the camera mount not to interrupt light paths of the irradiation light and the reflection light.

16. A semiconductor package testing apparatus comprising:

a inclined illuminator installed above a measurement target and having a hemispheric shape, the inclined illuminator having a plurality of light emitting diodes (LEDs) disposed on a portion other than an opening formed in the center thereof to supply inclined illumination to the measurement target;

an inclined image capture unit configured to receive reflection light reflected by the measurement target and capture a side image of the measurement target;

a reflection mirror installed at a tilt angle on one side of the inclined image capture unit to guide the reflection light reflected by the measurement target into the inclined image capture unit; and a condensing lens installed in front of the inclined image capture unit and configured to condense incident reflection light.

17. The apparatus of claim 16, wherein the measurement target is a multi-stack package (MSP) in which a ball land to which a solder ball is bonded is formed on a first surface of a printed circuit board (PCB) and the solder ball is bonded to the ball land during a reflow process and functions as an input/output terminal of the PCB, and the inclined image capture unit is installed at a predetermined tilt angle with an optical axis of reflection light re-reflected by the reflection mirror to capture an image of a contact portion between the solder ball and the ball land.

18. The apparatus of claim 17, further comprising an optical angle shifter disposed between the inclined image capture unit and the condensing lens and configured to shift a direction of the reflection light, wherein when reflection light reflected at two spots of the measurement target is re-reflected by the reflection mirror and incident to the inclined image capture unit, the optical angle shifter compensates for a difference in length between two light paths starting from the two spots.

19. The apparatus of claim 18, wherein the inclined image capture unit obtains light reflected from the surface of the measurement target as color information, extracts a red (R) value and a blue (B) value from the color information, and determines whether or not the solder ball is bonded to the ball land based on the color information, when the solder ball and the ball land are in a wet state, the solder ball formed of lead (Pb) melts during a reflow process and is bonded to the ball land formed of copper (Cu) and the ball land formed of the copper is concealed so that subtracting the B value from the R value gives a critical value or lower, and when the solder ball and the ball land are in a non-wet state, the solder ball formed of lead does not melt during the reflow process and the ball land formed of the copper is exposed so that subtracting the B value from the R value gives a value higher than a critical value, and the critical value ranges from 0 to 255 on condition of 8 bits.

20. A testing apparatus, comprising:

a first illumination device to illuminate a target area of a tested device, the first illumination device providing illumination to the target area such that light from the first illumination device contacts the target area along an axis parallel to a center length axis of the tested device;

a second illumination device to illuminate a target area of a tested device, the second illumination device providing illumination to the target area such that light from the second illumination device contacts the target area along an axis that is not parallel to a center length axis of the tested device, the second illumination device including:

a substantially dome-shaped structure having a hole at a peak of the dome to permit light to pass through the hole; and a plurality of light emitting diodes mounted to an inside surface of the dome-shape structure;

a first image capture device to receive light from the first illumination device reflected off of the target area; and a second image capture device to receive light from the second illumination device reflected off of the target area, wherein the center length axis of the tested device defines a first direction.

21. The testing apparatus according to claim 20, wherein the second image capture device includes a color-receptive image capture device.

22. The testing apparatus according to claim 20, wherein the first illumination device comprises:

a substantially flat plate; and a plurality of light emitting diodes mounted to the plate.

23. The testing apparatus according to claim 20, further comprising a beam-splitting mirror positioned along a light path between the first illumination device and the target area, to reflect light from the first illumination device toward the target area, and to pass light from the target area toward the first image capture device.

24. The testing apparatus according to claim 23, wherein the beam-splitting mirror is positioned at a 45° angle with respect to the first direction.

25. The testing apparatus according to claim 20, further comprising:

a mirror to reflect light that has been reflected off of the target area from an inclined angle to be parallel with respect to the first direction, the mirror reflecting the light from the tested device toward the second image capture device.

26. The testing apparatus according to claim 25, further comprising:

a condensing lens to receive and condense the light from the mirror; and an optical angle shifter to receive the condensed light from the condensing lens, and to adjust the light to provide a focused image to an image-reception end of the second image capture device, wherein the second image-capture unit is positioned to have a center length axis that is not parallel to the first direction.

27. The testing apparatus according to claim 20, further comprising a case, wherein the first and second illumination devices and first and second image capture devices are mounted to be located on an inside of the case and to be fixed with respect to the case.

28. The testing apparatus according to claim 27, further comprising a camera mounting structure having a height less than a height of the case, wherein the first and second image capture devices are mounted to an inner surface of a top side of the camera mounting structure.

29. The testing apparatus according to claim 27, further comprising an illumination unit mounting structure mounted to an inside surface of a lower portion of the case, wherein the first and second illumination devices are mounted to the illumination unit mounting structure.

* * * * *